US010113973B2

(12) United States Patent
Yang

(10) Patent No.: US 10,113,973 B2
(45) Date of Patent: Oct. 30, 2018

(54) INFRARED INK PRINT TESTING FOR MANUFACTURING

(71) Applicant: Microsoft Technology Licensing, LLC, Redmond, WA (US)

(72) Inventor: Qingsheng Jason Yang, Redmond, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 0 days.

(21) Appl. No.: 15/719,257

(22) Filed: Sep. 28, 2017

(65) Prior Publication Data

US 2018/0209912 A1 Jul. 26, 2018

Related U.S. Application Data

(60) Provisional application No. 62/448,873, filed on Jan. 20, 2017.

(51) Int. Cl.
*G01J 5/02* (2006.01)
*G01N 21/84* (2006.01)
(Continued)

(52) U.S. Cl.
CPC ......... *G01N 21/8422* (2013.01); *G01N 21/59* (2013.01); *G01N 33/32* (2013.01);
(Continued)

(58) Field of Classification Search
CPC ............. C09D 175/16; G01N 21/8422; G01N 21/8806; G01N 2021/3568;
(Continued)

(56) References Cited

U.S. PATENT DOCUMENTS 4,302,108 A * 11/1981 Timson .............. G01N 21/8901 250/341.3
5,500,732 A * 3/1996 Ebel .................. G01M 11/0264 356/124

(Continued)

OTHER PUBLICATIONS

Orlove, Gary, "Easy IR Window Transmission Measurement", In Technical Publication of Infrared Training Center, Retrieved on: Jan. 12, 2017, 4 Pages.

(Continued)

*Primary Examiner* — Taeho Jo

(74) *Attorney, Agent, or Firm* — Alleman Hall Creasman & Tuttle LLP

(57) ABSTRACT

An assembly for testing an infrared (IR) ink print quality of an IR ink print area on an optical component includes a light source including an illuminated periphery and a dark interior, an IR camera having a field of view positioned to image the dark interior without imaging at least a portion of the illuminated periphery, and a component holder configured to hold the optical component between the IR camera and the light source such that IR light emitted from the portion of the illuminated periphery that illuminates the IR ink print area on the optical component is deflected into the field of view of the IR camera if the IR ink print area has defects but is not deflected into the field of view of the IR camera if the IR ink print area does not have defects.

20 Claims, 6 Drawing Sheets

200 206 208 218 220 212 202 214 210 216 204

(51) Int. Cl.
*G01N 33/32* (2006.01)
*G01N 21/59* (2006.01)
*C09D 11/50* (2014.01)

(52) U.S. Cl.
CPC ...... *C09D 11/50* (2013.01); *G01N 2021/8427* (2013.01); *G01N 2201/061* (2013.01)

(58) Field of Classification Search
CPC ........... G01N 2021/8427; G01N 21/35; G01N 21/892; G01N 21/95; G01N 21/95607; G01N 2201/105; G01N 25/00; G01N 33/32
USPC ........................................................ 250/341.1
See application file for complete search history.

(56) References Cited

U.S. PATENT DOCUMENTS 6,074,483 A 6/2000 Belotserkovsky et al.
6,504,625 B1 1/2003 Amero et al.
6,519,497 B1 * 2/2003 Blome .................. B23Q 17/24 700/114
6,542,622 B1 4/2003 Nelson et al.
6,744,050 B1 * 6/2004 Hornung ................. G07D 7/12 250/341.1
8,912,480 B2 12/2014 Pope et al.
8,957,380 B2 2/2015 Costello et al.
2004/0020992 A1 * 2/2004 Lasch .................... B32B 37/10 235/487
2006/0044341 A1 * 3/2006 Reichelsheimer .......................... G07B 17/00508 347/19
2006/0122059 A1 * 6/2006 Mathur ................... B41M 5/42 503/200
2007/0164117 A1 * 7/2007 Swiler ..................... B05D 5/06 235/491
2007/0258621 A1 * 11/2007 Kato ..................... G01B 11/24 382/100
2008/0090034 A1 4/2008 Harrison et al.
2008/0111074 A1 * 5/2008 Weir ...................... G01N 21/21 250/338.1
2008/0283757 A1 * 11/2008 Vahey .................. G01N 21/359 250/341.1
2011/0031318 A1 * 2/2011 Lasch ..................... B32B 37/10 235/491
2012/0235036 A1 9/2012 Hatakeyama et al.
2012/0258406 A1 * 10/2012 Rudolph ................... G03F 1/68 430/306
2013/0148089 A1 * 6/2013 Rudolph ................... G03F 1/68 355/30
2013/0293726 A1 * 11/2013 Armstrong-Muntner .................... G01M 11/005 348/187
2014/0098156 A1 * 4/2014 Taff ...................... B41J 2/04561 347/19
2014/0113116 A1 4/2014 Vienonen et al.
2014/0168304 A1 * 6/2014 Mizes ................. B41J 11/0015 347/14
2014/0218725 A1 * 8/2014 Lin ....................... G01N 21/94 356/239.8
2015/0103226 A1 * 4/2015 Takahashi ............. G02B 1/118 348/335
2015/0132550 A1 5/2015 Kohno et al.
2015/0199599 A1 * 7/2015 Morrill Web ............ B41M 3/14 235/488
2016/0054175 A1 2/2016 Jia et al.
2016/0195905 A1 7/2016 Wang
2016/0245916 A1 * 8/2016 Weber-Grabau ............................. H01J 37/32917
2017/0010211 A1 * 1/2017 Ohama ................ G01N 21/892
2018/0034557 A1 * 2/2018 Alpert .................. H04B 10/807

OTHER PUBLICATIONS

Travis, et al., “Determination of the Transmittance Uniformity of Optical Filter Standard Reference Materials”, In Journal of Research of the National Institute of Standards and Technology, vol. 100, No. 3, May 1995, pp. 241-256.

* cited by examiner

INFRARED INK PRINT TESTING FOR MANUFACTURING

CROSS REFERENCE TO RELATED APPLICATIONS

This application claims priority to U.S. Provisional Patent Application No. 62/448,873, filed Jan. 20, 2017, the entirety of which is hereby incorporated herein by reference.

BACKGROUND

Infrared (IR) ink may have optical properties that allow for a low transmittance of visible light and a high transmittance of IR light. As such, IR ink may be applied to a surface of a material that transmits IR light to hide an object positioned behind the material from view while still allowing IR light to pass through the material to the object. In one example, IR ink is applied to an interior surface of cover glass of a device that includes an IR camera. In particular, the IR ink is applied to a transmissive (e.g., see-through) camera window in an otherwise opaque bezel of the cover glass. The camera window is aligned with the IR camera to allow IR light to pass through the cover glass to the IR camera. The IR ink is applied to the camera window to hide the IR camera from view so that the opaque bezel has a uniform appearance. In this and other applications, defects in the IR ink can produce undesirable results, especially if the defects are not known.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

An assembly for testing an infrared (IR) ink print quality of an IR ink print area on an optical component includes a light source including an illuminated periphery and a dark interior, an IR camera having a field of view positioned to image the dark interior without imaging at least a portion of the illuminated periphery, and a component holder configured to hold the optical component between the IR camera and the light source such that IR light emitted from the portion of the illuminated periphery that illuminates the IR ink print area on the optical component is deflected into the field of view of the IR camera if the IR ink print area has defects but is not deflected into the field of view of the IR camera if the IR ink print area does not have defects.

DETAILED DESCRIPTION

Infrared (IR) ink may be applied as a coating to a surface of a material according to different printing processes. In one example, IR ink is applied to a surface of a material through a silk screen printing process. Before application of the IR ink via silk screening, the IR ink is mixed with thinner and hardener (e.g., retarder). After printing, the IR ink is baked dry. In another example, IR ink is applied to a surface of a material through an ink jet printing process. It will be appreciated that IR ink may be applied to a surface of a material according to any suitable printing process. Variations in such printing processes may affect print quality of the IR ink. Examples of printing process aspects that may affect the print quality include the IR ink mixture material properties, wear of the silk screen, distance, pressure, squeegee angle, speed, and screen tension. In some cases, such printing process variations may produce IR ink print defects. Example IR ink print defects include rough surfaces (e.g., orange peel), spots, dirt, pin holes, missing dot clusters (e.g., not circular), streaks, banding, scratches, abnormal shape (e.g., print is not a circle), discoloring (e.g., color non-uniformity), and transmittance failure (e.g., caused by out-of-spec ink mixture properties, print thickness and uniformity). Such IR ink print defects may reduce the IR performance of a device as well as negatively affect the aesthetics of the device.

Accordingly, the present disclosure is directed to an approach for testing the print quality of an IR ink print area on a planar surface of an optical component by measuring light scattering (i.e., haze) across the IR ink print area. In particular, IR ink print defects can generate haze and transmittance non-uniformity that degrade optical characteristics, such as image sharpness. As such, measuring haze of an IR ink print area on a planar surface of an optical component may be a suitable metric for testing IR ink print quality. Further, such an approach may be used to identify other types of IR ink print defects that degrade the IR ink performance both optically and aesthetically. This approach may be used to test an IR ink print area that is printed on a planar surface of an optical component according to any suitable printing process. Note that although the IR ink print area that is being tested is located on a planar surface of the optical component, a total shape of the optical component need not be planar.

Figure 1:
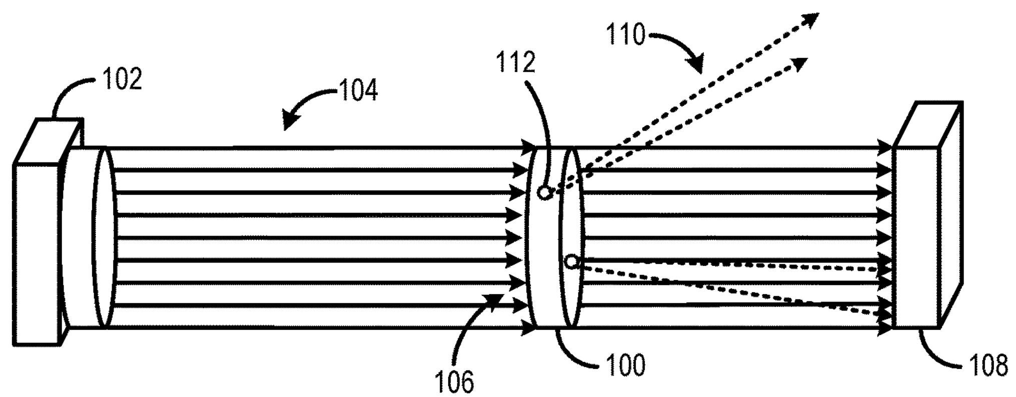
FIG. 1 schematically shows an example of haze in an infrared (IR) ink print area on an optical component.

Haze may be defined according to a standard (e.g., ASTM D1003-92 standard or its latest revisions D1003-00, D1003-07, D1003-13) as a ratio of light that is scattered by an optical component relative to light transmitted by the optical component. FIG. 1 schematically shows an example scenario in which an optical component 100 scatters incident light so that a direction of scattered light deviates more than a specified angle from a direction of the incident light, thereby creating haze according to the ASTM 1003-xx standards. A light source 102 directs collimated IR light 104 through an IR Ink print area 106 on the optical component 100. In the depicted example, the IR ink print area is the surface on the optical component facing the light source 102. An ideal IR ink print area would transmit all of the collimated IR light 104 received from the light source 102 through the optical component 100 to a light detector 108. However, the actual IR ink print area 106 scatters some IR light 110 (depicted by dotted lines) due to print defects, such as rough surface area and inhomogeneity in the IR ink medium etc. In the depicted example, IR light rays that hit a scattering artifact 112—i.e., a defect in the IR ink print area 106 are scattered in oblique directions. Such scattered IR light rays 110 are no longer collimated when those light rays hit the detector. Because all light emitted by the light source 102 is collimated, any area of the detector 108 that does not receive collimated light may be assumed to be light scattered due to defects in the IR ink print area 106 on the optical component 100. In one example, the standards define a haze value as the ratio between all scattered light from ±2.5° to ±90° to transmitted light inside a ±2.5° cone. In practice, IR ink print areas on optical components may exhibit some degree of haze and may have a haze value greater than 0. As such, an assessment of IR ink print quality may take this baseline degree of haze into consideration by using a haze value threshold, for example.

The optical component 100 may take any suitable form where the IR ink print area is located on a planar surface of the optical component. As discussed above, in some examples, the optical component may be light transmissive sheet that is coated with IR ink. In this example, the sheet is planar. In other examples, a total shape of the optical component may be nonplanar. The light source 102 may take any suitable form. In one example, the light source is a light emitting diode. In some examples, the light source may be a dual-band light source configured to emit IR light and visible light to illuminate the IR ink print area on the optical component. The light detector 108 may take any suitable form. In one example, the light detector is an IR camera. In some examples, the light detector may include an integration sphere. In some example, the light detector may be a dual-band light detector configured to detect IR light and visible light.

Figure 2:
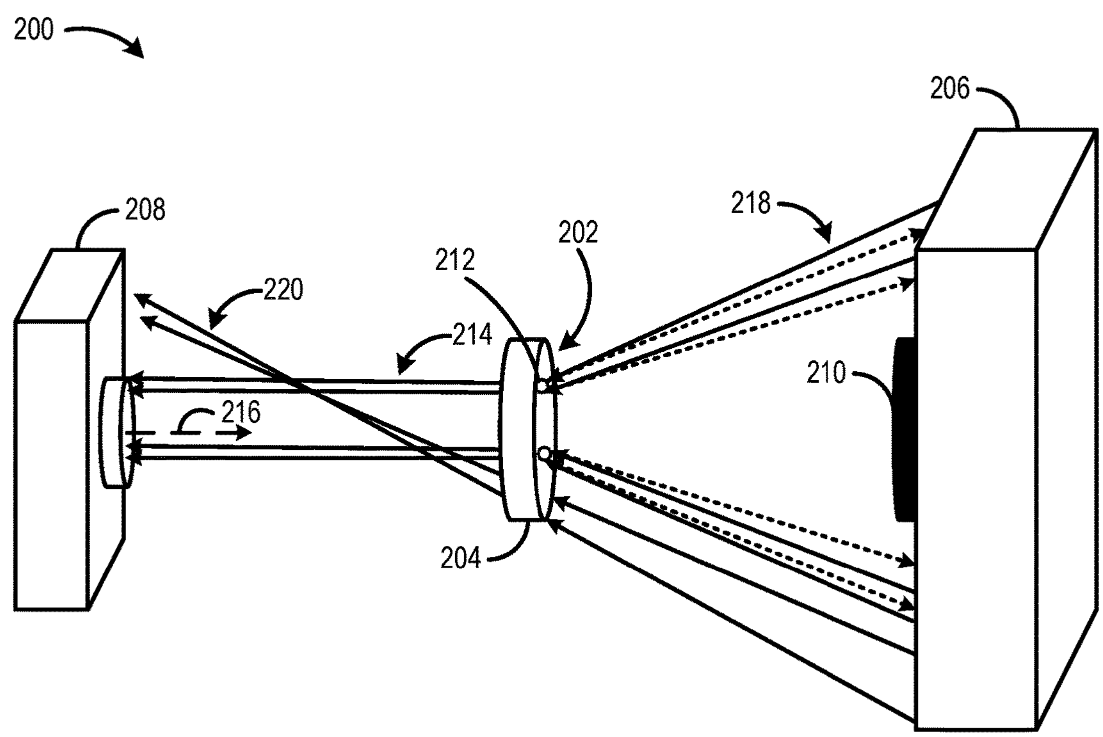
FIG. 2 schematically shows an example assembly for testing the print quality of an infrared (IR) ink print area on an optical component.

FIG. 2 schematically shows an example assembly 200 for testing the print quality of an IR ink print area 202 on an optical component 204 under test. The assembly 200 includes an IR light source 206 configured to emit IR light through the IR ink print area 202 on the optical component 204 in a reverse direction relative to the scenario illustrated in FIG. 1. In particular, the IR light source 206 is positioned upstream from the optical component 204 to emit IR light at different angles (e.g., oblique rays from multiple points on the light emitting surface) to illuminate the IR ink print area 202 on the optical component 204 with IR light. Note that the depicted IR light rays emitted from the IR light source 206 are provided as examples of the total amount of IR light emitted from the light source 206. In some actual examples, the IR ink print area 202 may be immersed in IR light that is emitted from the IR light source 206. Further, an IR light detector (e.g., IR camera) 208 is positioned downstream from the optical component 204 to detect IR light transmitted through the IR ink print area 202 on the optical component 204.

A light stop (or light block) 210 is coupled to the IR light source 206 in optical alignment with the IR ink print area 202 such that all paraxial light rays emitted from the light source 206 are blocked from hitting the IR ink print area 202 on the optical component 204. As used herein, paraxial light is the light that is parallel to an optical axis 216 of the IR light detector 208. Likewise, non-paraxial light is light that is not parallel to the optical axis 216 of the IR light detector 208. The paraxial light rays depicted in FIG. 2 correspond to the collimated IR light rays 104 that are emitted from the light source 102 of FIG. 1 albeit in reverse.

Because the light stop 210 blocks paraxial light rays emitted from the IR light source 206 from illuminating the IR ink print area, only non-paraxial IR light rays hit the scattering artifacts 212 of the IR ink print area 202. The IR light rays emitted from the IR light source 206 that are incident to the scattering artifacts 212 correspond to the scattered IR light rays 110 of FIG. 1 albeit in reverse. Accordingly, the scattering artifacts 212 direct the incident IR light rays 214 (e.g., through diffraction, reflection, and/or refraction) such that the IR light rays 214 are parallel (or near parallel) to the optical axis 216 of the IR light detector 208 upon exiting the optical component 204. On the other hand, non-paraxial light rays 220 emitted from the IR light source 206 that illuminate a region of the IR ink print area 202 without any defects pass through the IR ink print area 202 without being deflected or otherwise changing direction more than standard refraction, and thus miss the IR light detector 208 and are not detected by the IR light detector 208.

In some implementations, the assembly 200 may include light collection optics positioned intermediate the optical component 204 and the IR light detector 208. The light collection optics may be configured to receive light deflected by the scattering artifacts 212 at non-paraxial angles and redirect the received light into the FOV of the IR light detector 208 such that the light may add to the total signal detected by the IR light detector that corresponds to the haze value of the optical component. In at least some implementations, the collection optics can be configured to map a defect region to a particular camera pixel throughout a range of different scatter angles.

The light stop 210 may be made from any suitable material having low IR reflectance characteristics. By constructing the light stop 210 from such material, the light stop 210 can absorb the paraxial light rays emitted from the light source 206 in order to avoid multiple light reflections that could interfere with analysis of the IR ink print area. In one example, the light stop 210 is made of Bakelite material.

Figure 3:
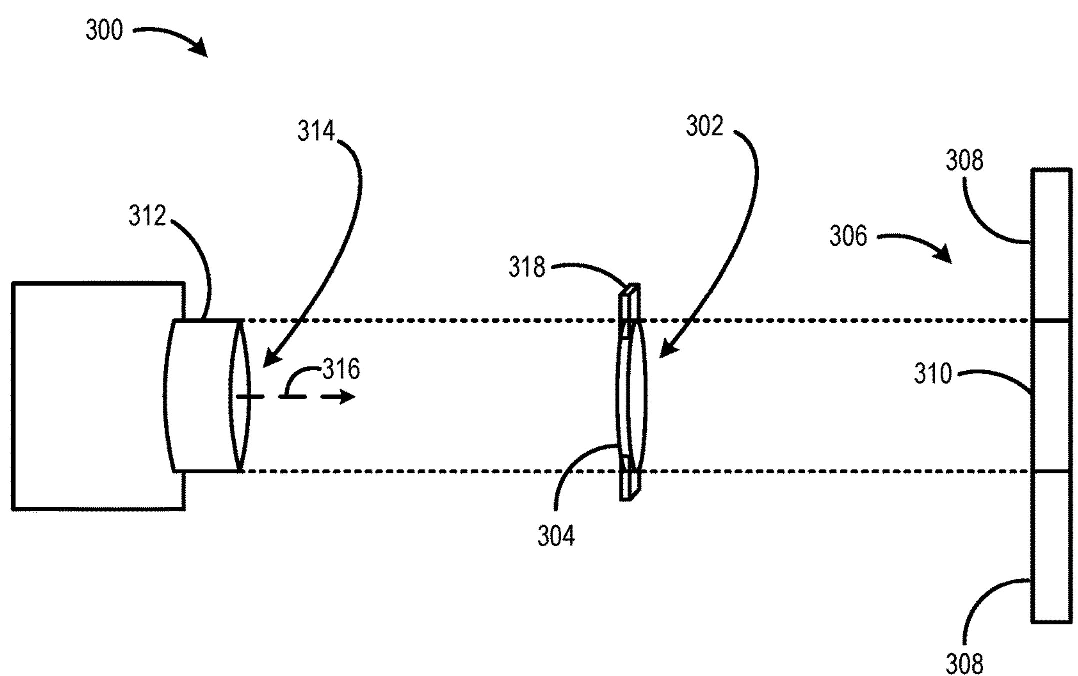
FIG. 3 schematically shows another example assembly for testing the print quality of an IR ink print area on an optical component.

FIG. 3 shows another example assembly 300 for testing the print quality of an IR ink print area 302 on an optical component 304. The assembly 300 includes an IR light source 306 including an illuminated periphery 308 and a dark interior 310. No light is emitted from the dark interior 310. According to such a configuration, in some examples, the IR light source 306 may emit IR light that appears to be an illuminated ring that corresponds to the shape of the illuminated periphery 308.

The assembly 300 further includes an IR light detector in the form of an IR camera 312 having a field of view (FOV) 314 positioned to image the dark interior 310 of the IR light source 306. Additional apertures may be added to define the field of view. Opaque areas completely surrounding the IR ink on the optical component may also be used as such an aperture. Note that in such examples the IR camera is focused at the IR ink print. The IR camera 312 and the IR light source 306 may have fixed positions relative to one another. For example, an optical axis 316 of the IR camera may be optically aligned with a center point of the interior dark 310 of the IR light source 306. The IR camera 312 may be optically aligned with the IR light source 306 in any suitable manner.

A component holder 318 is configured to hold the optical component 304 between the IR camera 312 and the IR light source 306 such that the IR ink print area 302 is optically aligned with the dark interior 310 and further with the FOV 314 of the IR camera 312. The component holder 318 may position the optical component 304 such that defects (e.g., scattering artifacts) in the IR ink print area 302 on the optical component 304 deflect IR light emitted from the illuminated periphery 308 of the IR light source 306 into the FOV 314 of the IR camera 312.

In the illustrated implementation, the IR camera 312 is positioned such that the FOV 314 does not image non-deflected light from the illuminated periphery 308 of the IR light source 306. In other words, only IR light that is deflected in a direction parallel to an optical axis 316 of the IR camera 312 by the scattering artifacts in the IR ink print area 302 are detected by the IR camera 312. As such, the total signal collected by the IR camera 312 from light transmitted through the IR ink print area 302 corresponds to the total amount of haze in the IR ink print area 302 on the optical component 304.

The component holder 318 may hold the optical component 304 in any suitable manner and may take any suitable form. In examples where the optical component is substantially flat, such as an optical sheet, the component holder may be configured to clamp opposing sides of the sheet along a periphery to hold the sheet in a fixed position. In other examples, the component holder may at least partially surround an edge/perimeter on the optical component to form a frame that holds the optical component.

In some examples, the IR camera 312 may be configured such that the FOV 314 only images the dark interior 310 and does not image the illuminated periphery 308 of the IR light source 306. In other examples, the FOV 314 of the IR camera 312 may be sized to image an area larger than the dark interior 310 including a portion of the illuminated periphery 308. In such examples, the IR camera 312 may not image at least a portion of the illuminated periphery 308. In such examples, IR light detected in the FOV 314 that is outside of the dark interior 310, such as light from the illuminated periphery 308, may appear as a bright halo in an image produced by the IR camera 312. In this case, the bright halo may be ignored or subtracted from a resulting image that is analyzed for purposes of assessing IR ink print quality.

In some implementations, the FOV 314 of the IR camera 312 may be sized to image an entirety of the IR ink print area 302. In yet other implementations, the FOV 314 of the IR camera 312 may be sized to image only a portion of the IR ink print area 302. In some such implementations, the position on the optical component 304 may be adjusted relative to the component holder 318 and/or the assembly 300 in order to image all of the different portions of the IR ink print area 302 for IR ink print quality testing purposes. In other such implementations, the component holder 318 may be configured to automatically move the optical component 304 to different positions, and temporarily hold the optical component 304 at each position in order to perform an IR ink print quality test on each different portion of the IR ink print area 302.

In some implementations, the IR light source 306 may be configured such that the dark interior 310 is not illuminated and thus does not need blocking via a light stop. In other implementations, such as shown in FIG. 2, the IR light source includes a light source configured to emit IR light behind the light stop or another type of IR light blocking element that forms the dark interior. In particular, the IR light stop may be configured to prevent paraxial IR light emitted by the light source from reaching the IR ink print area on the optical component.

In some implementations, the IR camera 312 may be a dual-band camera configured to detect IR light and visible light. The dual-band camera may be configured to output IR light images based on the detected IR light and output visible light images based on the detected visible light.

Figure 4A:
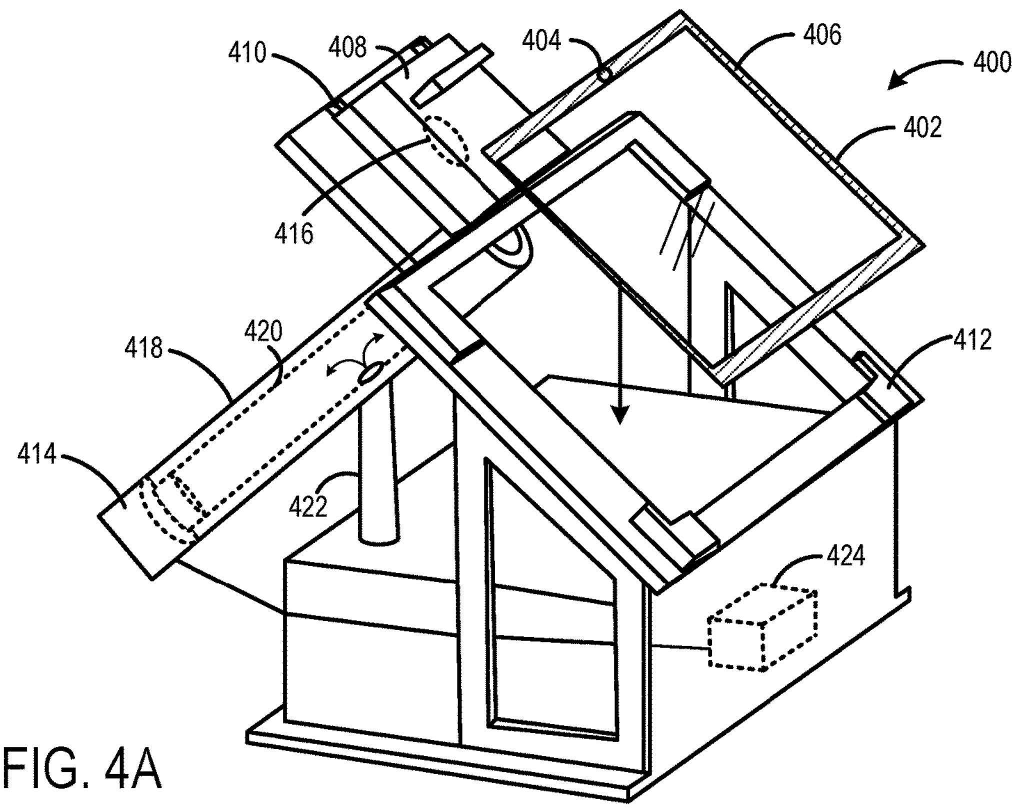
FIGS. 4A-4B show an example device configured to test the print quality of an IR ink print area on an optical component.
Figure 4B:
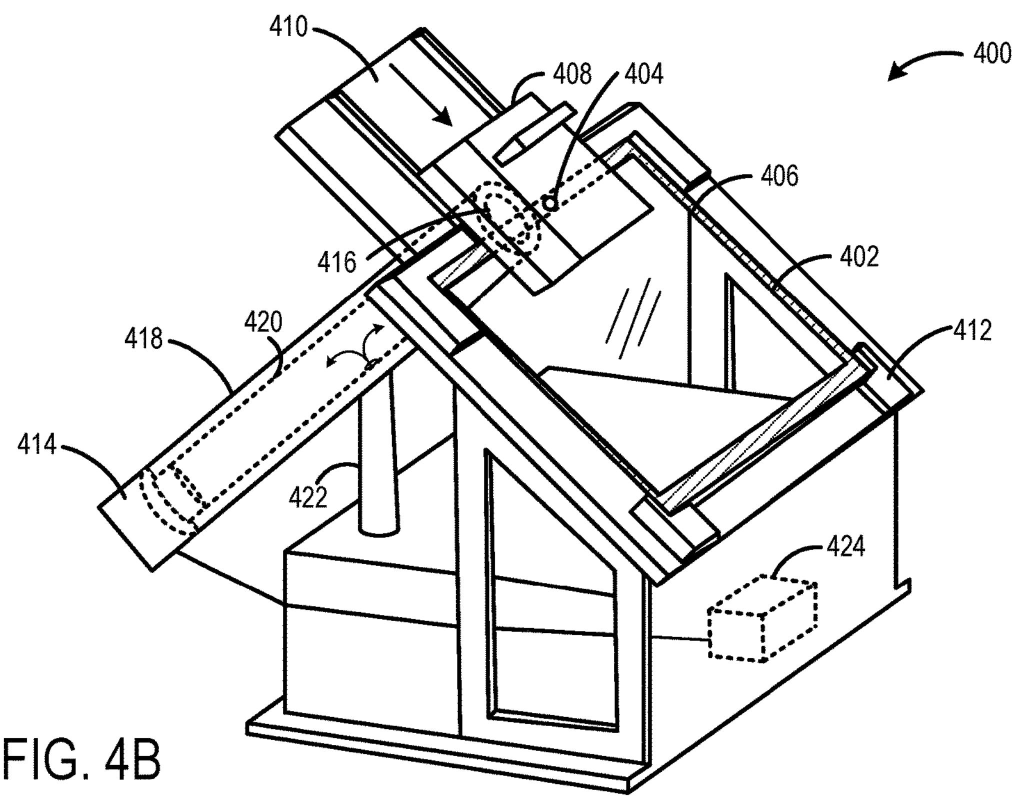

FIGS. 4A-4B show an example device 400 configured to test the print quality of an IR ink print area on an optical component 402 under test. In the depicted example, the optical component 402 is a cover glass sheet for a device, such as a laptop or tablet. In this example, IR ink is applied to an interior surface of the cover glass sheet to create a transmissive (e.g., see-through) camera window 404 in an otherwise opaque bezel 406 of the cover glass sheet 402. The camera window 404 may be aligned with an IR camera of the device to allow IR light to pass through the cover glass sheet 402 to the IR camera. The IR ink is applied to the camera window 404 to hide the IR camera from view so that the opaque bezel 406 has a uniform appearance.

The device 400 includes an LED light panel 408 that acts as an IR light source to illuminate the IR ink print area 404 on the optical component 402 under test with non-paraxial light. The LED light panel 408 may be slidable along a frame 410 to allow for installation of the optical component 402 under test into the device 400. In FIG. 4A, the LED light panel 408 may be moved to an upward position on the frame 410 to allow for clearance to install the optical component 402 in a component holder 412 that maintains the optical component 402 in a fixed position. The component holder 412 includes clamps that hold the corners of the cover glass sheet to maintain the cover glass sheet 402 in a fixed position in the device 400. As shown in FIG. 4B, once the optical component 402 under test is installed in the component holder 412, the LED light panel 408 may be moved along the frame 410 to a downward position.

In one example, the LED light panel 408 is a dual-band, flat-panel, light source that can emit IR light and/or visible light. In some implementations where the light source is dual-band, the light source can operate in either a “dark field” or a “bright field” mode. In “dark field” mode, the light source is slid to a position to provide non-paraxial IR light to the dual-band camera. In “bright field” mode, the light source is slid to a position to provide paraxial visible light to the dual-band camera. Moreover, the LED light panel 408 may be configured to emit visible light when operating in an optical component calibration mode. In the calibration mode, the visible light may be emitted from the LED light panel 408, imaged by a camera 414, and the image may be presented on a display such that an operator of the device 400 can view the image on the display in order to properly align the cover glass sheet 402 in the component holder 412. Once the cover glass sheet 402 is installed in the component holder 412, the LED light panel 408 may be switched to an optical component testing mode in which the LED light panel 408 emits IR light to illuminate the IR ink print area 404. Note that in other examples, a dual-band light source can be a broadband light source that has spectral contents in both visible and IR ranges.

The LED light panel 408 includes a light stop 416 configured to block paraxial light emitted from the LED light panel 408 from illuminating the IR ink print area 404 on the optical component 402 under test. The light stop 416 may be positioned on the surface of the LED light panel 408 such that it is optically aligned with the IR ink print area 404 on the optical component 402 under test and optically aligned with an optical axis of the camera 414. The diameter of the light stop may be sized in accordance with a field of view of the camera and/or a size of the IR ink print area.

In one example, the light stop 416 is an aluminum disk that is anodized matte black with no texturing. For example, the aluminum disk may be taped or glued directly to the surface of the LED light panel 408 to secure the disk in a desired fixed position. In another example, the light stop 416 is made of black Bakelite or another type of plastic that has very low IR reflectance to inhibit light multi-reflection.

In some implementations, the light stop 416 is one of a plurality of interchangeable light stops that are removably affixable to the LED light source 408. The plurality of interchangeable light stops may be differently sized to correspond to a plurality of different optical components testable by the device 400. For example, the different light stops may have different diameters that correspond to different size IR windows printed on different cover glass sheets.

The camera 414 acts as an IR light detector configured to detect IR light transmitted by scattering artifacts of the IR ink print area 404 on the optical component 402 under test. If there are no defects in the IR ink print area 404 then ideally the camera 414 would not detect any IR light emitted from the LED light source 408, or detect only a halo of light around the dark field. The camera 414 may be positioned in the device 400 such that an optical axis of the camera 414 is optically aligned with the IR ink print area 404 and the light stop 416 when the optical component 402 is installed in the device 400 and the LED light source 408 is moved to the downward position on the frame 410.

In some implementations, the camera 414 may have a field of view (FOV) that is sized to substantially match the IR ink print area 404 on the optical component 402 under test and/or the light stop 416 that establishes a dark interior of the LED light source 408. In some example, the camera 414 may be fitted with a macro lens having a FOV that matches the light stop 416. In other examples, the camera 414 may image a portion of the LED light source 408. In such examples, IR light detected by the camera 414 that is outside of the dark interior of the light stop 416 may appear as a bright halo in an image produced by the camera 414. In this case, the bright halo may be ignored or subtracted from the resulting image that is analyzed for purposes of assessing IR ink print quality of the IR ink print area 404.

In some examples, the camera 414 is a dual-band light detector configured to detect IR light and visible light. In some examples, the dual-band light detector may output visible light images when operating in the optical component calibration mode. The visible light images may be presented on a display such that an operator of the device 400 can view the visible light images on the display in order to properly align the cover glass sheet 402 in the component holder 412. Once the cover glass sheet 402 is installed in the component holder 412, the light detector may be switched to an optical component testing mode in which the light detector outputs IR images for print quality analysis of the IR ink print area 404. For example, the dual-band light detector may output IR images that are analyzed to detect haze and other defects that are revealed by the detected IR light. Furthermore, in some examples, the dual-band light detector may output visible light images for print quality analysis of the IR ink print area 404 when operating in the optical component testing mode. For example, the visible light images output by the dual-band light detector may reveal defects that are not revealed by the IR images, such as regions in the IR ink print area 404 where IR ink is not present or where a layer of IR ink is too thin.

The camera 414 is positioned at the end of a light-absorption tunnel 418 that has an interior surface 420 that is coated with an IR light absorbing coating. The light-absorption tunnel 418 may be employed to absorb any non-paraxial light that is coincidentally directed towards the camera 414. The camera 414 and the light-absorption tunnel 418 have a fixed position that is optically aligned with the LED light panel 408, and more particularly the light stop 416, when the LED light panel 408 is situated in the downward position on the frame 410. The component holder 412 may be positioned intermediate the LED light panel 408 and the camera 414 such that when the LED light panel 408 illuminates the IR ink print area 404 on the optical component 402 under test, IR light that is directed by scattering artifacts at an angle parallel to the optical axis of the camera 414 is detected by the camera 414 to form an IR image. In particular, if the IR ink print area 404 on the optical component 402 is perfectly homogeneous without any scattering, then theoretically the camera 414 would image a flat black image that does not include any light from the light source 408 (or a ring of light around the dark field). On the other hand, if the IR ink print area has any scattering artifacts or other defects, such as local non-uniformity or optical discontinuities caused by impurity, particles, and silk screen wearing etc., IR light rays that hit those scattering artifacts from non-paraxial angles (oblique rays from multiple points) will be directed (through diffraction, reflection, and refraction) into the FOV of the camera 414 and show up in the IR image as bright spots. Consequently, the IR image may have small bright features and a dark background. Scattered light may appear as grey to white features (e.g., spots and patches) in the IR image. Note that in this example the LED light panel is operating in a dark field mode.

The device 400 includes an air blower 422 configured to provide clean air to the optical component 402 under test and the other components of the device (e.g., camera 414, tunnel 418) in order to clean away any debris that could interfere with testing. In some examples, the clean air may be ionized. The air blower 422 may be configured to provide ionizing air to blow particles and dust off the surface of the optical component 402 and the components of the device 400. The air blower 422 may allow the device 400 to operate in a standard room instead of requiring clean room conditions.

The device 400 is in communication with one or more cooperating computer(s) 424 configured to receive images from the camera 414 and analyze the received images to identify features of scattering artifacts and assess the quality of the IR ink print area 404 on an optical component 402 under test. In some examples, the computer 424 may be configured to locate the IR ink print area in the IR image, perform background subtraction, determine image statistics of the IR ink print area (e.g., globally and/or for a local sliding window), perform image segmentation and feature extraction, calculate a decision function to determine the print quality of the IR ink print area, and/or report and log the results and visualizations of the test. In some examples, the computer 424 may be configured to calculate image statistics and integrated density to determine a total haze value/reading. In some examples, computer 424 may be configured to extract details of the image features, such as pinholes via a blob tool. In some examples, the computer 424 may be configured to apply a set of test thresholds to determine a pass or fail assessment for the optical component 402 under test.

In some implementations, the computer 424 may be configured to filter out signals produced by other layers in an optical stack on the optical component 402 under test. In one example, the optical component includes anti-smudge coating, glass substrate, and IR ink film. The anti-smudge coating and the glass substrate can generate low level and consistent scattering that forms a common background signal in images produced by the camera 414. Therefore, in the image analysis, the computer 424 may be configured to filter the background signal prior to performing the quality assessment. On the other hand, if the device 400 performs the quality assessment of the whole cover glass stack at the IR ink aperture, the background subtraction step may be skipped.

In some implementations, the device 400 may be configured to test different shaped IR ink print areas of different optical components. For example, a diameter of the light stop and the DUT holder 412 may be adjusted to change the alignment of the device 400 to accommodate a different sized IR ink print area.

Figure 5:
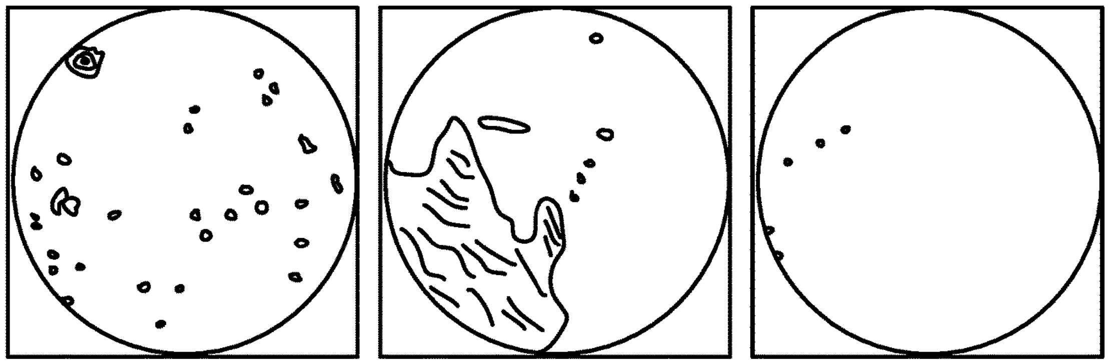
FIGS. 5, 6, and 7 show example images of IR ink print area samples produced by the device of FIGS. 4A-4B.
Figure 6:
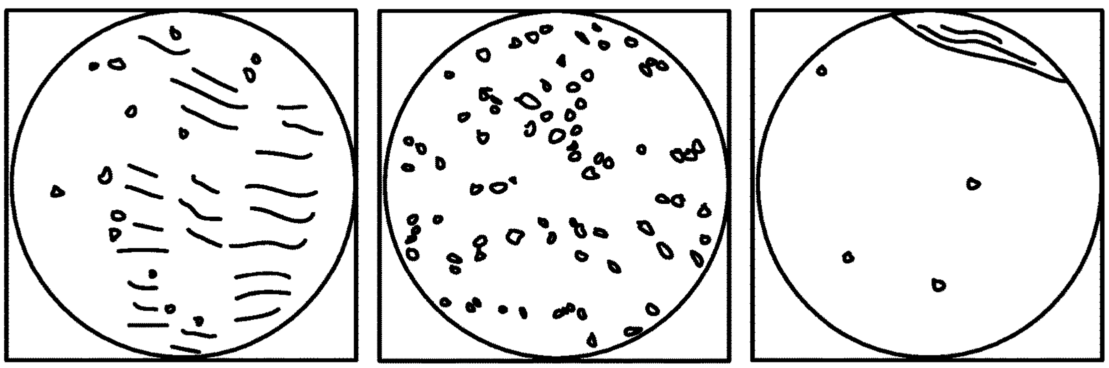
Figure 7:
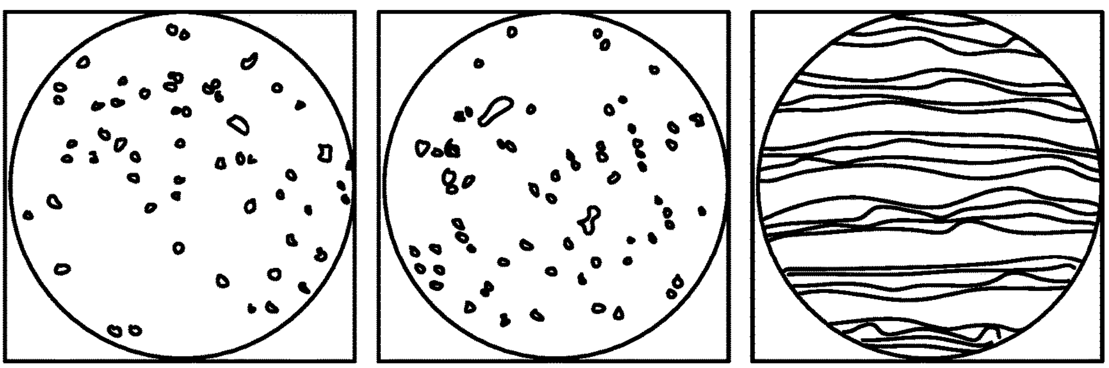

FIGS. 5-7 schematically show example IR images of IR ink print area samples produced by the device 400 of FIGS. 4A-4B. While the images are shown with defects on white fields, it should be understood that actual dark field images, as described above, will have white to gray defects on a black field. In FIG. 5, the left image shows an IR ink print area that includes spots resulting from printing defects, the middle image shows an IR ink print area that includes scrapping resulting from printing defects, and the right image shows an IR ink print area that has minimal defects. In FIG. 6, the left image shows an IR ink print area that includes rub defects resulting from printing defects. The middle image shows an IR ink print area that includes speckling resulting from printing defects. The right image shows an IR ink print area that includes a boarder deformation resulting from printing defects. FIG. 7 shows three images of different IR ink print areas that include defects due to finger prints.

The IR images produced by the IR camera of the device 400 may provide powerful visualization of the IR ink print quality that may be used to improve the IR ink printing process to produce higher quality optical components.

Figure 8:
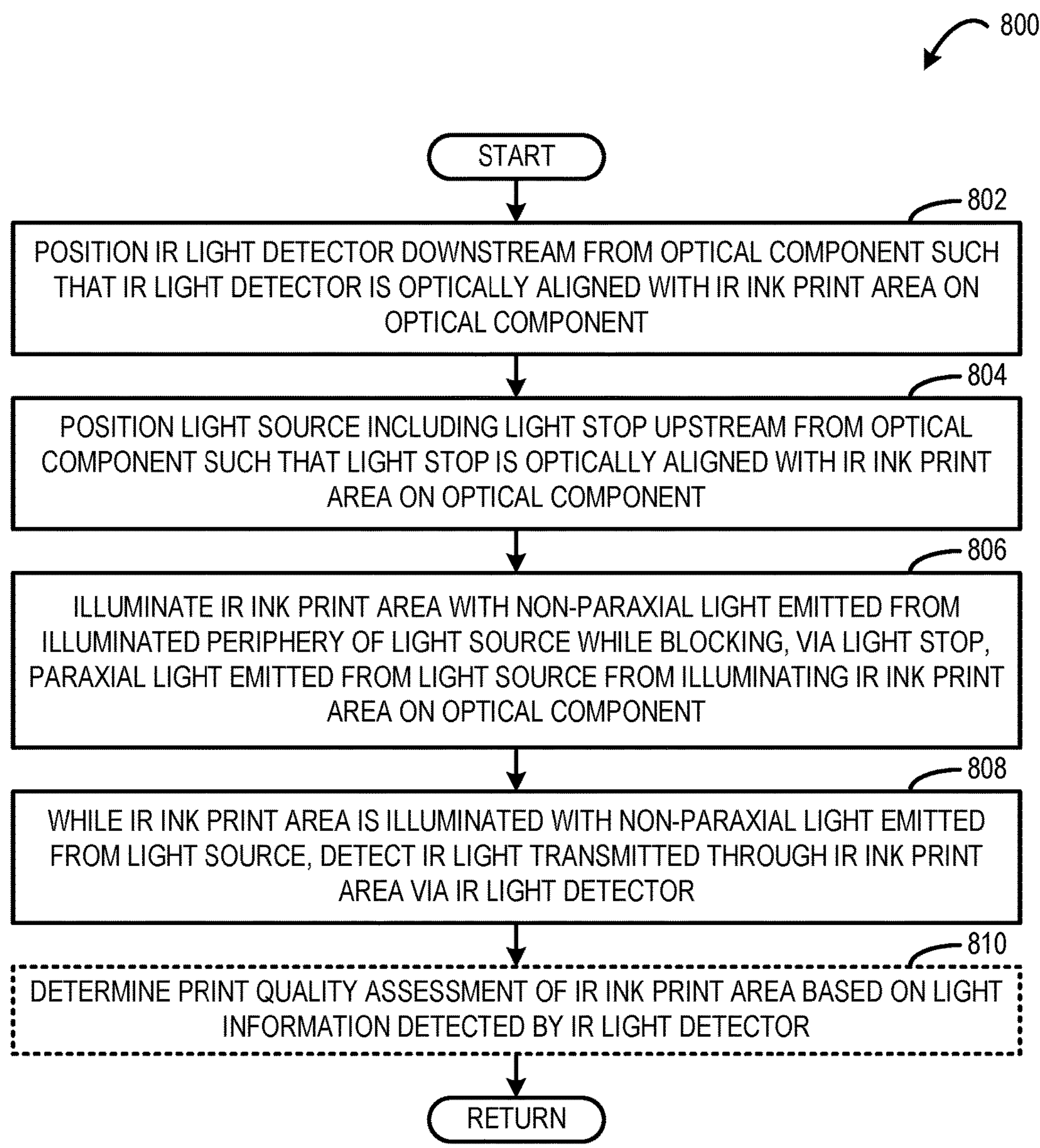
FIG. 8 shows an example method for testing the print quality of an IR ink print area on an optical component.

FIG. 8 shows an example method 800 for testing the print quality of an IR ink print area on an optical component under test by measuring light scattered by the IR ink print area. For example, the method 800 may be performed using the device 400 shown in FIGS. 4A and 4B.

At 802, the method 800 includes positioning an IR light detector downstream from the optical component such that an optical axis of the IR light detector is optically aligned with the IR ink print area of the optical component.

At 804, the method 800 includes positioning a light source including a light stop upstream from the optical component such that the light stop is optically aligned with the optical axis of the IR light detector. The light stop is configured to block paraxial light emitted from the light source in parallel with the optical axis of the IR light detector from illuminating the IR ink print area of the optical component. In some examples, the light stop is configured to match a shape of the IR ink print area and/or a field of view of an IR light detector.

At 806, the method includes illuminating the IR ink print area on the optical component with non-paraxial IR light from the upstream light source (e.g., from an illuminated periphery of the light source) while blocking, via the light stop, paraxial light from the light source from illuminating the IR ink print area (or not illuminating the IR ink print area with paraxial light from the light source).

At 808, the method 800 includes, while the IR ink print area is illuminated with non-paraxial light from the light source, detecting IR light transmitted through the IR ink print area, via the IR light detector. The IR light detected by the IR light detector represents haze that may diminishes the print quality of the IR ink print area on the optical component.

At 810, the method 800 optionally may include determining, via a computing system, a print quality assessment of the IR ink print area on the optical component based on IR light transmitted through the IR ink print area and detected by the IR light detector. For example, the computing system may analyze IR images produced by the IR light detector. In some examples, determining the print quality assessment of the IR ink print area may include locating the IR ink print area in an IR image produced by the IR light detector, performing background subtraction, determining image statistics (e.g., integrated density used to determine a total haze value/reading) of the IR ink print area, performing image segmentation and feature extraction (e.g., pinholes using a blob tool), and calculating a decision function (e.g., to apply a set of test thresholds to determine a pass or fail assessment) to determine the print quality of the IR ink print area.

In some implementations, the methods and processes described herein may be tied to a computing system of one or more computing devices. In particular, such methods and processes may be implemented as a computer-application program or service, and/or other computer-program product.

Figure 9:
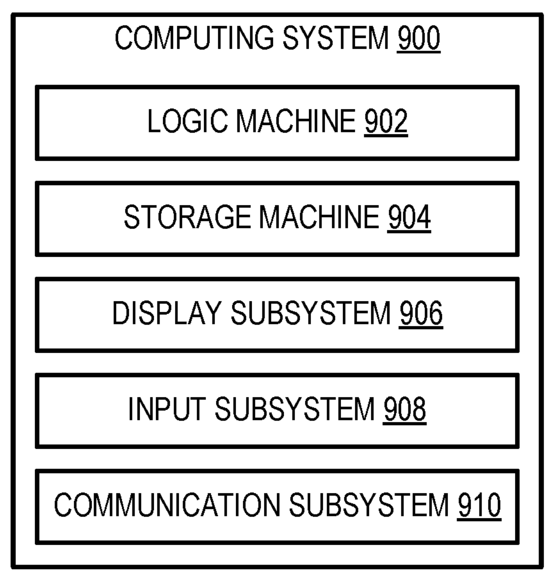
FIG. 9 schematically shows an example computing system.

FIG. 9 schematically shows a non-limiting implementation of a computing system 900 that can enact one or more of the methods and processes described above. Computing system 900 is shown in simplified form. Computing system 900 may take the form of one or more personal computers, server computers, tablet computers, network computing devices, mobile computing devices, mobile communication devices (e.g., smart phone), and/or other computing devices. For example, computer 424 is an example of computing system 900.

Computing system 900 includes a logic machine 902 and a storage machine 904. Computing system 900 may optionally include a display subsystem, an input subsystem, a communication subsystem, and/or other components not shown in FIG. 9.

Logic machine 902 includes one or more physical devices configured to execute instructions. For example, the logic machine may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

The logic machine 902 may include one or more processors configured to execute software instructions. Additionally or alternatively, the logic machine 902 may include one or more hardware or firmware logic machines configured to execute hardware or firmware instructions. Processors of the logic machine 902 may be single-core or multi-core, and the instructions executed thereon may be configured for sequential, parallel, and/or distributed processing. Individual components of logic machine 902 optionally may be distributed among two or more separate devices, which may be remotely located and/or configured for coordinated processing. Aspects of logic machine 902 may be virtualized and executed by remotely accessible, networked computing devices configured in a cloud-computing configuration.

Storage machine 904 includes one or more physical devices configured to hold instructions executable by logic machine 902 to implement the methods and processes described herein. When such methods and processes are implemented, the state of storage machine 904 may be transformed—e.g., to hold different data.

Storage machine 904 may include removable and/or built-in devices. Storage machine 904 may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. Storage machine 904 may include volatile, nonvolatile, dynamic, static, read/write, read-only, random-access, sequential-access, location-addressable, file-addressable, and/or content-addressable devices.

It will be appreciated that storage machine 904 includes one or more physical devices. However, aspects of the instructions described herein alternatively may be propagated by a communication medium (e.g., an electromagnetic signal, an optical signal, etc.) that is not held by a physical device for a finite duration.

Aspects of logic machine 902 and storage machine 904 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

When included, display subsystem 906 may be used to present a visual representation of data held by storage machine 904. This visual representation may take the form of a graphical user interface (GUI). As the herein described methods and processes change the data held by the storage machine, and thus transform the state of the storage machine, the state of the display subsystem 906 may likewise be transformed to visually represent changes in the underlying data. Display subsystem 906 may include one or more display devices utilizing virtually any type of technology. Such display devices may be combined with logic machine 902 and/or storage machine 904 in a shared enclosure, or such display devices may be peripheral display devices.

When included, input subsystem 908 may comprise or interface with one or more user-input devices such as a keyboard, mouse, touch screen, touch pad, or game controller. In some implementations, input subsystem 908 may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity.

When included, communication subsystem 910 may be configured to communicatively couple computing system 900 with one or more other computing devices. Communication subsystem 910 may include wired and/or wireless communication devices compatible with one or more different communication protocols. As non-limiting examples, communication subsystem 910 may be configured for communication via a wireless telephone network, or a wired or wireless local- or wide-area network. In some implementations, communication sub system 910 may allow computing system 900 to send and/or receive messages to and/or from other devices via a network such as the Internet.

In an example, an assembly for testing an infrared (IR) ink print quality of an IR ink print area on an optical component comprises a light source including an illuminated periphery and a dark interior, an IR camera having a field of view positioned to image the dark interior without imaging at least a portion of the illuminated periphery, and a component holder configured to hold the optical component between the IR camera and the light source such that IR light emitted from the portion of the illuminated periphery that illuminates the IR ink print area on the optical component is deflected into the field of view of the IR camera if the IR ink print area has defects but is not deflected into the field of view of the IR camera if the IR ink print area does not have defects. In this example and/or other examples, IR light emitted from the illuminated periphery may be deflected to the IR camera by regions of the IR ink print area that include a defect, and IR light emitted from the illuminated periphery that may not be deflected to the IR camera by regions of the IR ink print area that do not include a defect. In this example and/or other examples, the field of view of the IR camera may not image the illuminated periphery. In this example and/or other examples, the dark interior of the light source may be formed from a light stop coupled to the light source and configured to block IR light from being emitted from the IR light source. In this example and/or other examples, the IR light source may be configured to emit no IR light from the dark interior. In this example and/or other examples, the defects in the IR ink print area may deflect IR light in parallel with an optical axis of the IR camera. In this example and/or other examples, the illuminated periphery of the light source may be configured to illuminate the IR ink print area on the optical component with non-paraxial IR light that is not parallel with an optical axis of the IR camera. In this example and/or other examples, the light source may be a dual-band light source configured to emit IR light and visible light, and the IR camera may be a dual-band camera configured to output IR images and visible light images. In this example and/or other examples, a computing system configured to determine a print quality assessment of the IR ink print area based on IR light transmitted through the IR ink print area and detected by the IR camera. In this example and/or other examples, the assembly may further comprise a light-absorption tunnel positioned intermediate the IR camera and the component holder, the light-absorption tunnel including an interior surface configured to absorb incident non-paraxial light that is not parallel with an optical axis of the IR camera.

In an example, a device configured to test a IR ink print quality of an IR ink print area on an optical component comprises a component holder configured to hold the optical component in a fixed position, a light source configured to emit IR light to illuminate the IR ink print area on the optical component, an IR light detector configured to detect IR light exiting from the IR ink print area on the optical component in parallel with an optical axis of the IR light detector, and a light stop positioned between the light source and the IR ink print area on the optical component and configured to prevent paraxial IR light emitted from the light source in parallel with the optical axis of the IR light detector from illuminating the IR ink print area on the optical component while allowing non-paraxial IR light emitted from the light source that is not parallel with the optical axis of the IR light detector to illuminate the IR ink print area on the optical component. In this example and/or other examples, IR light emitted from the light source may be deflected into a field of view of the IR light detector if the IR ink print area has defects but may not be deflected into the field of view of the IR light detector if the IR ink print area does not have defects. In this example and/or other examples, IR light emitted from the light source may be deflected into the field of view of the IR light detector by regions of the IR ink print area that include a defect, and IR light emitted from the light source may not be deflected into the field of view of the IR light detector by regions of the IR ink print area that do not include a defect. In this example and/or other examples, the light stop may be one of a plurality of interchangeable light stops that are configured to be removably affixable to the light source and differently sized to correspond to a plurality of different optical components testable by the device. In this example and/or other examples, the light source may be a dual-band light source configured to emit IR light and visible light, and the IR light detector may be a dual-band camera configured to output IR images and visible light images. In this example and/or other examples, the device may further comprise a light-absorption tunnel positioned intermediate the IR light detector and the component holder, the light-absorption tunnel including an interior surface configured to absorb incident non-paraxial light that is not parallel with the optical axis of the IR light detector. In this example and/or other examples, the IR light detector may include an IR camera having a field of view sized to match a size of the light stop. In this example and/or other examples, the device may further comprise a computing system configured to determine a print quality assessment of the IR ink print area based on IR light transmitted through the IR ink print area and detected by the IR light detector.

In an example, a method for testing an IR ink print quality of an IR ink print area on an optical component comprises positioning an IR light detector downstream from the optical component such that an optical axis of the IR light detector is optically aligned with the IR ink print area, positioning a light source including a light stop upstream from the optical component such that the light stop is optically aligned with the optical axis of the IR light detector, illuminating the IR ink print area on the optical component with non-paraxial IR light emitted from the light source while blocking, via the light stop, paraxial IR light emitted from the light source from illuminating the IR ink print area on the optical component, wherein the paraxial IR light is parallel with the optical axis of the IR light detector and the non-paraxial IR light is not parallel with the optical axis of the IR light detector, and while the IR ink print area is illuminated with non-paraxial IR light from the light source, detecting IR light transmitted through the IR ink print area, via the IR light detector. In this example and/or other examples, the method may further comprises determining, via a computing system, a print quality assessment of the IR ink print area based on IR light transmitted through the IR ink print area and detected by the IR light detector.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. An assembly for testing an infrared (IR) ink print quality of an IR ink print area on an optical component, the assembly comprising:

a light source including an illuminated periphery and a dark interior;

an IR camera having a field of view positioned to image the dark interior without imaging at least a portion of the illuminated periphery; and a component holder configured to hold the optical component between the IR camera and the light source such that IR light emitted from the portion of the illuminated periphery that illuminates the IR ink print area on the optical component is deflected into the field of view of the IR camera if the IR ink print area has defects but is not deflected into the field of view of the IR camera if the IR ink print area does not have defects.

2. The assembly of claim 1, wherein IR light emitted from the illuminated periphery is deflected to the IR camera by regions of the IR ink print area that include a defect, and wherein IR light emitted from the illuminated periphery is not deflected to the IR camera by regions of the IR ink print area that do not include a defect.

3. The assembly of claim 1, wherein the field of view of the IR camera does not image the illuminated periphery.

4. The assembly of claim 1, wherein the dark interior of the light source is formed from a light stop coupled to the light source and configured to block IR light from being emitted from the IR light source.

5. The assembly of claim 1, wherein the IR light source is configured to emit no IR light from the dark interior.

6. The assembly of claim 1, wherein the defects in the IR ink print area deflect IR light in parallel with an optical axis of the IR camera.

7. The assembly of claim 1, wherein the illuminated periphery of the light source is configured to illuminate the IR ink print area on the optical component with non-paraxial IR light that is not parallel with an optical axis of the IR camera.

8. The assembly of claim 1, wherein the light source is a dual-band light source configured to emit IR light and visible light, and wherein the IR camera is a dual-band camera configured to output IR images and visible light images.

9. The assembly of claim 1, further comprising:

a computing system configured to determine a print quality assessment of the IR ink print area based on IR light transmitted through the IR ink print area and detected by the IR camera.

10. The assembly of claim 1, further comprising:

a light-absorption tunnel positioned intermediate the IR camera and the component holder, the light-absorption tunnel including an interior surface configured to absorb incident non-paraxial light that is not parallel with an optical axis of the IR camera.

11. A device configured to test a IR ink print quality of an IR ink print area on an optical component, the device comprising:

a component holder configured to hold the optical component in a fixed position;

a light source configured to emit IR light to illuminate the IR ink print area on the optical component;

an IR light detector configured to detect IR light exiting from the IR ink print area on the optical component in parallel with an optical axis of the IR light detector; and a light stop positioned between the light source and the IR ink print area on the optical component and configured to prevent paraxial IR light emitted from the light source in parallel with the optical axis of the IR light detector from illuminating the IR ink print area on the optical component while allowing non-paraxial IR light emitted from the light source that is not parallel with the optical axis of the IR light detector to illuminate the IR ink print area on the optical component.

12. The device of claim 11, wherein IR light emitted from the light source is deflected into a field of view of the IR light detector if the IR ink print area has defects but is not deflected into the field of view of the IR light detector if the IR ink print area does not have defects.

13. The device of claim 12, wherein IR light emitted from the light source is deflected into the field of view of the IR light detector by regions of the IR ink print area that include a defect, and wherein IR light emitted from the light source is not deflected into the field of view of the IR light detector by regions of the IR ink print area that do not include a defect.

14. The device of claim 11, wherein the light stop is one of a plurality of interchangeable light stops that are configured to be removably affixable to the light source and differently sized to correspond to a plurality of different optical components testable by the device.

15. The device of claim 11, wherein the light source is a dual-band light source configured to emit IR light and visible light, and wherein the IR light detector is a dual-band camera configured to output IR images and visible light images.

16. The device of claim 11, further comprising:

a light-absorption tunnel positioned intermediate the IR light detector and the component holder, the light-absorption tunnel including an interior surface configured to absorb incident non-paraxial light that is not parallel with the optical axis of the IR light detector.

17. The device of claim 11, wherein the IR light detector includes an IR camera having a field of view sized to match a size of the light stop.

18. The device of claim 11, further comprising:

a computing system configured to determine a print quality assessment of the IR ink print area based on IR light transmitted through the IR ink print area and detected by the IR light detector.

19. A method for testing an IR ink print quality of an IR ink print area on an optical component, the method comprising:

positioning an IR light detector downstream from the optical component such that an optical axis of the IR light detector is optically aligned with the IR ink print area;

positioning a light source including a light stop upstream from the optical component such that the light stop is optically aligned with the optical axis of the IR light detector;

illuminating the IR ink print area on the optical component with non-paraxial IR light emitted from the light source while blocking, via the light stop, paraxial IR light emitted from the light source from illuminating the IR ink print area on the optical component, wherein the paraxial IR light is parallel with the optical axis of the IR light detector and the non-paraxial IR light is not parallel with the optical axis of the IR light detector; and while the IR ink print area is illuminated with non-paraxial IR light from the light source, detecting IR light transmitted through the IR ink print area, via the IR light detector.

20. The method of claim 19, further comprising:

determining, via a computing system, a print quality assessment of the IR ink print area based on IR light transmitted through the IR ink print area and detected by the IR light detector.

* * * * *